United States Patent [19]

Schiller

[11] Patent Number: 5,602,099

[45] Date of Patent: Feb. 11, 1997

[54] δ OPIOID RECEPTOR ANTAGONISTS

[75] Inventor: Peter Schiller, Montreal, Canada

[73] Assignee: Aktiebolaget Astra, Sodertalje, Sweden

[21] Appl. No.: 176,938

[22] Filed: Jan. 4, 1994

[30] Foreign Application Priority Data

Jan. 5, 1993 [SE] Sweden .................... 9300012

[51] Int. Cl.$^6$ ............................. A61K 38/07
[52] U.S. Cl. ..................... 514/18; 514/15; 514/16; 514/17; 530/328; 530/329; 530/330
[58] Field of Search ............ 514/18, 19, 15–17; 530/330, 331, 334, 329, 320

[56] References Cited

PUBLICATIONS

Schiller, et al., in *Peptides: Chemistry, Structure and Biology*, Hodges and Smith, Eds., ESCOM, Leiden, pp. 483–486 (1994).
Schiller, et al., *J. Med. Chem.* 35, pp. 3956–3961 (1992).
Schiller, et al., *J. Med. Chem.* 36, pp. 3182–3187 (1993).
Schiller, et al. (1992) "Differential stereochemical requirements of mu vs delta opioid receptors . . . " *Proceedings of the National Academy of Sciences, U.S.A.* 89:11871.
Schiller, et al. (1992) *Chemical Abstracts*, 117:19235p "Conformationally restricted deltorphin analogs . . . ".
Portoghese, et al., (1988) "Application of the message . . . " 31: 281–282.
Portoghese, et al. (1991) "An approach to the design of receptor–type–selective non–peptide antagonists . . . " 34:1757–762.
Cotton, et al. (1984) "ICI 174864: a highly selective antagonist . . . " 97:331–332.
Schiller, et al. (1992) "A new class of potent and highly selective . . . " Abstract in *FASEB J.* 6:A1575.
Hermanson, *Immobilized Affinity Ligand Techniques*, 137–141 & 146, (1992).

*Primary Examiner*—David Lukton
*Attorney, Agent, or Firm*—White & Case

[57] ABSTRACT

The invention concerns compounds of the formula 1

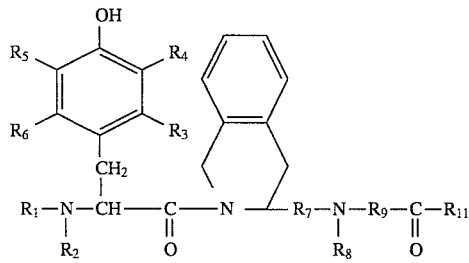

and pharmaceutical compositions containing the compounds as active ingredients. The peptides of the invention are δ opioid receptor antagonists and are useful as analgesics and immunosuppressants.

10 Claims, No Drawings

SEQUENCE LISTING ( 1 ) GENERAL INFORMATION:

( i i i ) NUMBER OF SEQUENCES: 35

( 2 ) INFORMATION FOR SEQ ID NO:1:

( i ) SEQUENCE CHARACTERISTICS:
        ( A ) LENGTH: 5 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /note= "N,N-diallyltyrosine"

( i x ) FEATURE:
        ( A ) NAME/KEY: Modified-site
        ( B ) LOCATION: 2
        ( D ) OTHER INFORMATION: /label= Aib
            / note= "α-aminoisobutyric acid"

( i x ) FEATURE:
        ( A ) NAME/KEY: Modified-site
        ( B ) LOCATION: 3
        ( D ) OTHER INFORMATION: /label= Aib
            / note= "α-aminoisobutyric acid"

( x i ) SEQUENCE DESCRIPTION: SEQ ID NO:1:

Tyr  Xaa  Xaa  Phe  Leu
  1                        5

( 2 ) INFORMATION FOR SEQ ID NO:2:

( i ) SEQUENCE CHARACTERISTICS:
        ( A ) LENGTH: 4 amino acids ( B ) TYPE: amino acid
            ( D ) TOPOLOGY: linear ( i i ) MOLECULE TYPE: peptide ( i x ) FEATURE:
            ( A ) NAME/KEY: Modified-site
            ( B ) LOCATION: 2
            ( D ) OTHER INFORMATION: /label= Tic
                    / note= "1,2,3,4-tetrahydroisoquinoline-3-carboxylic acid"

( i x ) FEATURE:
            ( A ) NAME/KEY: Modified-site
            ( B ) LOCATION: 3
            ( D ) OTHER INFORMATION: /label= Hfe
                    / note= "Homophenylalanine"

( x i ) SEQUENCE DESCRIPTION: SEQ ID NO:2:

Tyr  Xaa  Xaa  Phe
    1

( 2 ) INFORMATION FOR SEQ ID NO:3:

( i ) SEQUENCE CHARACTERISTICS:
            ( A ) LENGTH: 4 amino acids
            ( B ) TYPE: amino acid
            ( D ) TOPOLOGY: linear ( i i ) MOLECULE TYPE: peptide ( i x ) FEATURE:
            ( A ) NAME/KEY: Modified-site
            ( B ) LOCATION: 2
            ( D ) OTHER INFORMATION: /label= Tic$\psi$[CH$_2$—..
                    / note= "3-methyl-1,2,3,4-tetrahydroisoquinoline"

( i x ) FEATURE:
            ( A ) NAME/KEY: Region
            ( B ) LOCATION: 2..3
            ( D ) OTHER INFORMATION: /note= "nonpeptidyl bond"

( x i ) SEQUENCE DESCRIPTION: SEQ ID NO:3:

Tyr  Xaa  Phe  Phe
    1

( 2 ) INFORMATION FOR SEQ ID NO:4:

( i ) SEQUENCE CHARACTERISTICS:
            ( A ) LENGTH: 4 amino acids
            ( B ) TYPE: amino acid
            ( D ) TOPOLOGY: linear ( i i ) MOLECULE TYPE: peptide ( i x ) FEATURE:
            ( A ) NAME/KEY: Modified-site
            ( B ) LOCATION: 2
            ( D ) OTHER INFORMATION: /label= Tic
                    / note= "1,2,3,4-tetrahydroisoquinoline-3-carboxylic acid"

( x i ) SEQUENCE DESCRIPTION: SEQ ID NO:4:

Tyr  Xaa  Phe  Phe
    1

( 2 ) INFORMATION FOR SEQ ID NO:5:

( i ) SEQUENCE CHARACTERISTICS:
            ( A ) LENGTH: 4 amino acids
            ( B ) TYPE: amino acid
            ( D ) TOPOLOGY: linear ( i i ) MOLECULE TYPE: peptide ( i x ) FEATURE:

(A) NAME/KEY: Modified-site
(B) LOCATION: 2
(D) OTHER INFORMATION: /label= Tic
/ note= "1,2,3,4-tetrahydroisoquinoline-3-carboxylic acid"

(ix) FEATURE:
(A) NAME/KEY: Modified-site
(B) LOCATION: 4
(D) OTHER INFORMATION: /note= "Phe—NH$_2$ (phenylalanine amide)"

(xi) SEQUENCE DESCRIPTION: SEQ ID NO:5:

Tyr Xaa Phe Phe
1

(2) INFORMATION FOR SEQ ID NO:6:

(i) SEQUENCE CHARACTERISTICS:
(A) LENGTH: 4 amino acids
(B) TYPE: amino acid
(D) TOPOLOGY: linear (ii) MOLECULE TYPE: peptide (ix) FEATURE:
(A) NAME/KEY: Modified-site
(B) LOCATION: 1
(D) OTHER INFORMATION: /note= "Tyr(N$^\alpha$Me), i.e., N$^\alpha$- methyltyrosine"

(ix) FEATURE:
(A) NAME/KEY: Modified-site
(B) LOCATION: 2
(D) OTHER INFORMATION: /label= Tic
/ note= "1,2,3,4-tetrahydroisoquinoline-3-carboxylic acid"

(xi) SEQUENCE DESCRIPTION: SEQ ID NO:6:

Tyr Xaa Phe Phe
1

(2) INFORMATION FOR SEQ ID NO:7:

(i) SEQUENCE CHARACTERISTICS:
(A) LENGTH: 4 amino acids
(B) TYPE: amino acid
(D) TOPOLOGY: linear (ii) MOLECULE TYPE: peptide (ix) FEATURE:
(A) NAME/KEY: Modified-site
(B) LOCATION: 1
(D) OTHER INFORMATION: /note= "Tyr(N$^\alpha$Cpm), i.e., N$^\alpha$- cyclopropylmethyltyrosine"

(ix) FEATURE:
(A) NAME/KEY: Modified-site
(B) LOCATION: 2
(D) OTHER INFORMATION: /label= Tic
/ note= "1,2,3,4-tetrahydroisoquinoline-3-carboxylic acid"

(xi) SEQUENCE DESCRIPTION: SEQ ID NO:7:

Tyr Xaa Phe Phe
1

(2) INFORMATION FOR SEQ ID NO:8:

(i) SEQUENCE CHARACTERISTICS:
(A) LENGTH: 4 amino acids
(B) TYPE: amino acid
(D) TOPOLOGY: linear (ii) MOLECULE TYPE: peptide (ix) FEATURE:

(A) NAME/KEY: Modified-site
(B) LOCATION: 1
(D) OTHER INFORMATION: /note= "Tyr(N$^\alpha$Hex),
    i.e., N$^\alpha$- hexyltyrosine"

(ix) FEATURE:
(A) NAME/KEY: Modified-site
(B) LOCATION: 2
(D) OTHER INFORMATION: /label= Tic
    / note= "1,2,3,4-tetrahydroisoquinoline-3-carboxylic acid"

(xi) SEQUENCE DESCRIPTION: SEQ ID NO:8:

Tyr Xaa Phe Phe
1

(2) INFORMATION FOR SEQ ID NO:9:

(i) SEQUENCE CHARACTERISTICS:
    (A) LENGTH: 4 amino acids
    (B) TYPE: amino acid
    (D) TOPOLOGY: linear (ii) MOLECULE TYPE: peptide (ix) FEATURE:
    (A) NAME/KEY: Modified-site
    (B) LOCATION: 1
    (D) OTHER INFORMATION: /note= "Tyr(N$^\alpha$Et$_2$),
        i.e., N$^\alpha$- diethyltyrosine"

(ix) FEATURE:
    (A) NAME/KEY: Modified-site
    (B) LOCATION: 2
    (D) OTHER INFORMATION: /label= Tic
        / note= "1,2,3,4-tetrahydroisoquinoline-3-carboxylic acid"

(xi) SEQUENCE DESCRIPTION: SEQ ID NO:9:

Tyr Xaa Phe Phe
1

(2) INFORMATION FOR SEQ ID NO:10:

(i) SEQUENCE CHARACTERISTICS:
    (A) LENGTH: 4 amino acids
    (B) TYPE: amino acid
    (D) TOPOLOGY: linear (ii) MOLECULE TYPE: peptide (ix) FEATURE:
    (A) NAME/KEY: Modified-site
    (B) LOCATION: 1
    (D) OTHER INFORMATION: /label= Dmt
        / note= "2,6-dimethyltyrosine"

(ix) FEATURE:
    (A) NAME/KEY: Modified-site
    (B) LOCATION: 2
    (D) OTHER INFORMATION: /label= Tic
        / note= "1,2,3,4-tetrahydroisoquinoline-3-carboxylic acid"

(xi) SEQUENCE DESCRIPTION: SEQ ID NO:10:

Tyr Xaa Phe Phe
1

(2) INFORMATION FOR SEQ ID NO:11:

(i) SEQUENCE CHARACTERISTICS:
    (A) LENGTH: 4 amino acids
    (B) TYPE: amino acid
    (D) TOPOLOGY: linear (ii) MOLECULE TYPE: peptide ( i x ) FEATURE:
          ( A ) NAME/KEY: Modified-site
          ( B ) LOCATION: 1
          ( D ) OTHER INFORMATION: /label= Dmt
                    / note= "2,6-dimethyltyrosine"

( i x ) FEATURE:
          ( A ) NAME/KEY: Modified-site
          ( B ) LOCATION: 2
          ( D ) OTHER INFORMATION: /label= Tic
                    / note= "1,2,3,4-tetrahydroisoquinoline-3-carboxylic acid"

( i x ) FEATURE:
          ( A ) NAME/KEY: Modified-site
          ( B ) LOCATION: 4
          ( D ) OTHER INFORMATION: /note= "Phe—NH$_2$ (phenylalanine amide)"

( x i ) SEQUENCE DESCRIPTION: SEQ ID NO:11:

Tyr  Xaa  Phe  Phe
1

( 2 ) INFORMATION FOR SEQ ID NO:12:

( i ) SEQUENCE CHARACTERISTICS:
               ( A ) LENGTH: 4 amino acids
               ( B ) TYPE: amino acid
               ( D ) TOPOLOGY: linear ( i i ) MOLECULE TYPE: peptide ( i x ) FEATURE:
               ( A ) NAME/KEY: Modified-site
               ( B ) LOCATION: 1
               ( D ) OTHER INFORMATION: /label= Tyr(3-F)
                         / note= "3-fluorotyrosine"

( i x ) FEATURE:
               ( A ) NAME/KEY: Modified-site
               ( B ) LOCATION: 2
               ( D ) OTHER INFORMATION: /label= Tic
                         / note= "1,2,3,4-tetrahydroisoquinoline-3-carboxylic acid"

( x i ) SEQUENCE DESCRIPTION: SEQ ID NO:12:

Tyr  Xaa  Phe  Phe
1

( 2 ) INFORMATION FOR SEQ ID NO:13:

( i ) SEQUENCE CHARACTERISTICS:
               ( A ) LENGTH: 4 amino acids
               ( B ) TYPE: amino acid
               ( D ) TOPOLOGY: linear ( i i ) MOLECULE TYPE: peptide ( i x ) FEATURE:
               ( A ) NAME/KEY: Modified-site
               ( B ) LOCATION: 1
               ( D ) OTHER INFORMATION: /label= Tyr(3-Cl)
                         / note= "3-chlorotyrosine"

( i x ) FEATURE:
               ( A ) NAME/KEY: Modified-site
               ( B ) LOCATION: 2
               ( D ) OTHER INFORMATION: /label= Tic
                         / note= "1,2,3,4-tetrahydroisoquinoline-3-carboxylic acid"

( x i ) SEQUENCE DESCRIPTION: SEQ ID NO:13:

Tyr  Xaa  Phe  Phe
1

( 2 ) INFORMATION FOR SEQ ID NO:14:

( i ) SEQUENCE CHARACTERISTICS:

(A) LENGTH: 4 amino acids
(B) TYPE: amino acid
(D) TOPOLOGY: linear (ii) MOLECULE TYPE: peptide (ix) FEATURE:
(A) NAME/KEY: Modified-site
(B) LOCATION: 1
(D) OTHER INFORMATION: /label= Tyr(3-Br)
/ note= "3-bromotyrosine"

(ix) FEATURE:
(A) NAME/KEY: Modified-site
(B) LOCATION: 2
(D) OTHER INFORMATION: /label= Tic
/ note= "1,2,3,4-tetrahydroisoquinoline-3-carboxylic acid"

(xi) SEQUENCE DESCRIPTION: SEQ ID NO:14:

Tyr Xaa Phe Phe
1

(2) INFORMATION FOR SEQ ID NO:15:

(i) SEQUENCE CHARACTERISTICS:
(A) LENGTH: 4 amino acids
(B) TYPE: amino acid
(D) TOPOLOGY: linear (ii) MOLECULE TYPE: peptide (ix) FEATURE:
(A) NAME/KEY: Modified-site
(B) LOCATION: 1
(D) OTHER INFORMATION: /label= Dmt
/ note= "2,6-dimethyltyrosine"

(ix) FEATURE:
(A) NAME/KEY: Modified-site
(B) LOCATION: 2
(D) OTHER INFORMATION: /label= Ticψ[CH$_2$—..
/ note= "3-methyl-1,2,3,4-tetrahydroisoquinoline"

(ix) FEATURE:
(A) NAME/KEY: Region
(B) LOCATION: 2..3
(D) OTHER INFORMATION: /note= "nonpeptidyl bond"

(xi) SEQUENCE DESCRIPTION: SEQ ID NO:15:

Tyr Xaa Phe Phe
1

(2) INFORMATION FOR SEQ ID NO:16:

(i) SEQUENCE CHARACTERISTICS:
(A) LENGTH: 4 amino acids
(B) TYPE: amino acid
(D) TOPOLOGY: linear (ii) MOLECULE TYPE: peptide (ix) FEATURE:
(A) NAME/KEY: Modified-site
(B) LOCATION: 1
(D) OTHER INFORMATION: /label= Dmt
/ note= "2,6-dimethyltyrosine"

(ix) FEATURE:
(A) NAME/KEY: Modified-site
(B) LOCATION: 2
(D) OTHER INFORMATION: /label= Ticψ[CH$_2$—..
/ note= "3-methyl-1,2,3,4-tetrahydroisoquinoline"

(ix) FEATURE:
(A) NAME/KEY: Modified-site
(B) LOCATION: 4

(D) OTHER INFORMATION: /note= "Phe—NH₂ (phenylalanine amide)"

(xi) SEQUENCE DESCRIPTION: SEQ ID NO:16:

Tyr Xaa Phe Phe
1

(2) INFORMATION FOR SEQ ID NO:17:

(i) SEQUENCE CHARACTERISTICS:
        (A) LENGTH: 4 amino acids
        (B) TYPE: amino acid
        (D) TOPOLOGY: linear (ii) MOLECULE TYPE: peptide (ix) FEATURE:
        (A) NAME/KEY: Modified-site
        (B) LOCATION: 2
        (D) OTHER INFORMATION: /label= Ticψ[CH₂—..
        / note= "3-methyl-1,2,3,4-tetrahydroisoquinoline"

(ix) FEATURE:
        (A) NAME/KEY: Modified-site
        (B) LOCATION: 3
        (D) OTHER INFORMATION: /label= ..-NCH₃]Phe
        / note= "N-methylphenylalanine"

(xi) SEQUENCE DESCRIPTION: SEQ ID NO:17:

Tyr Xaa Phe Phe
1

(2) INFORMATION FOR SEQ ID NO:18:

(i) SEQUENCE CHARACTERISTICS:
        (A) LENGTH: 4 amino acids
        (B) TYPE: amino acid
        (D) TOPOLOGY: linear (ii) MOLECULE TYPE: peptide (ix) FEATURE:
        (A) NAME/KEY: Modified-site
        (B) LOCATION: 2
        (D) OTHER INFORMATION: /label= Ticψ[CH₂—..
        / note= "3-methyl-1,2,3,4-tetrahydroisoquinoline"

(ix) FEATURE:
        (A) NAME/KEY: Modified-site
        (B) LOCATION: 3
        (D) OTHER INFORMATION: /label= ..—NH]Hfe
        / note= "Homophenylalanine"

(xi) SEQUENCE DESCRIPTION: SEQ ID NO:18:

Tyr Xaa Xaa Phe
1

(2) INFORMATION FOR SEQ ID NO:19:

(i) SEQUENCE CHARACTERISTICS:
        (A) LENGTH: 4 amino acids
        (B) TYPE: amino acid
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /label= Tyr(NMe)
        / note= "N-methyltyrosine"

(ix) FEATURE:
        (A) NAME/KEY: Modified-site
        (B) LOCATION: 2

( D ) OTHER INFORMATION: /label= Ticψ[CH$_2$—..
/ note= "3-methyl-1,2,3,4-tetrahydroisoquinoline"

( i x ) FEATURE:
( A ) NAME/KEY: Modified-site
( B ) LOCATION: 3
( D ) OTHER INFORMATION: /label= ..—NH]Hfe
/ note= "Homophenylalanine"

( x i ) SEQUENCE DESCRIPTION: SEQ ID NO:19:

Tyr Xaa Xaa Phe
1

( 2 ) INFORMATION FOR SEQ ID NO:20:

( i ) SEQUENCE CHARACTERISTICS:
( A ) LENGTH: 4 amino acids
( B ) TYPE: amino acid
( D ) TOPOLOGY: linear ( i i ) MOLECULE TYPE: peptide ( i x ) FEATURE:
( A ) NAME/KEY: Modified-site
( B ) LOCATION: 2
( D ) OTHER INFORMATION: /label= Tic
/ note= "1,2,3,4-tetrahydroisoquinoline-3-carboxylic acid"

( i x ) FEATURE:
( A ) NAME/KEY: Modified-site
( B ) LOCATION: 3
( D ) OTHER INFORMATION: /label= Phg
/ note= "phenylglycine"

( x i ) SEQUENCE DESCRIPTION: SEQ ID NO:20:

Tyr Xaa Gly Phe
1

( 2 ) INFORMATION FOR SEQ ID NO:21:

( i ) SEQUENCE CHARACTERISTICS:
( A ) LENGTH: 4 amino acids
( B ) TYPE: amino acid
( D ) TOPOLOGY: linear ( i i ) MOLECULE TYPE: peptide ( i x ) FEATURE:
( A ) NAME/KEY: Modified-site
( B ) LOCATION: 2
( D ) OTHER INFORMATION: /label= Tic
/ note= "1,2,3,4-tetrahydroisoquinoline-3-carboxylic acid"

( x i ) SEQUENCE DESCRIPTION: SEQ ID NO:21:

Tyr Xaa Trp Phe
1

( 2 ) INFORMATION FOR SEQ ID NO:22:

( i ) SEQUENCE CHARACTERISTICS:
( A ) LENGTH: 4 amino acids
( B ) TYPE: amino acid
( D ) TOPOLOGY: linear ( i i ) MOLECULE TYPE: peptide ( i x ) FEATURE:
( A ) NAME/KEY: Modified-site
( B ) LOCATION: 2
( D ) OTHER INFORMATION: /label= Tic
/ note= "1,2,3,4-tetrahydroisoquinoline-3-carboxylic acid"

( i x ) FEATURE:
( A ) NAME/KEY: Modified-site ( B ) LOCATION: 4
                    ( D ) OTHER INFORMATION: /note= "Phe—NH$_2$ (phenylalanine amide)"

( x i ) SEQUENCE DESCRIPTION: SEQ ID NO:22:

Tyr  Xaa  Trp  Phe
        1

( 2 ) INFORMATION FOR SEQ ID NO:23:

( i ) SEQUENCE CHARACTERISTICS:
                    ( A ) LENGTH: 4 amino acids
                    ( B ) TYPE: amino acid
                    ( D ) TOPOLOGY: linear ( i i ) MOLECULE TYPE: peptide ( i x ) FEATURE:
                    ( A ) NAME/KEY: Modified-site
                    ( B ) LOCATION: 2
                    ( D ) OTHER INFORMATION: /label= Tic
                            / note= "1,2,3,4-tetrahydroisoquinoline-3-carboxylic acid"

( x i ) SEQUENCE DESCRIPTION: SEQ ID NO:23:

Tyr  Xaa  His  Phe
        1

( 2 ) INFORMATION FOR SEQ ID NO:24:

( i ) SEQUENCE CHARACTERISTICS:
                    ( A ) LENGTH: 4 amino acids
                    ( B ) TYPE: amino acid
                    ( D ) TOPOLOGY: linear ( i i ) MOLECULE TYPE: peptide ( i x ) FEATURE:
                    ( A ) NAME/KEY: Modified-site
                    ( B ) LOCATION: 2
                    ( D ) OTHER INFORMATION: /label= Tic
                            / note= "1,2,3,4-tetrahydroisoquinoline-3-carboxylic acid"

( i x ) FEATURE:
                    ( A ) NAME/KEY: Modified-site
                    ( B ) LOCATION: 3
                    ( D ) OTHER INFORMATION: /label= 2- Nal
                            / note= "3-(2'-naphthyl)alanine"

( x i ) SEQUENCE DESCRIPTION: SEQ ID NO:24:

Tyr  Xaa  Ala  Phe
        1

( 2 ) INFORMATION FOR SEQ ID NO:25:

( i ) SEQUENCE CHARACTERISTICS:
                    ( A ) LENGTH: 4 amino acids
                    ( B ) TYPE: amino acid
                    ( D ) TOPOLOGY: linear ( i i ) MOLECULE TYPE: peptide ( i x ) FEATURE:
                    ( A ) NAME/KEY: Modified-site
                    ( B ) LOCATION: 2
                    ( D ) OTHER INFORMATION: /label= Tic
                            / note= "1,2,3,4-tetrahydroisoquinoline-3-carboxylic acid"

( i x ) FEATURE:
                    ( A ) NAME/KEY: Modified-site
                    ( B ) LOCATION: 3
                    ( D ) OTHER INFORMATION: /label= Atc
                            / note= "2-aminotetralin-2-carboxylic acid"

( x i ) SEQUENCE DESCRIPTION: SEQ ID NO:25:

Tyr Xaa Xaa Phe
1

( 2 ) INFORMATION FOR SEQ ID NO:26:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 2
        ( D ) OTHER INFORMATION: /label= Tic
            / note= "1,2,3,4-tetrahydroisoquinoline-3-carboxylic acid"

( i x ) FEATURE:
        ( A ) NAME/KEY: Modified-site
        ( B ) LOCATION: 4
        ( D ) OTHER INFORMATION: /label= Phe(pNO$_2$)
            / note= "4-nitrophenylalanine"

( x i ) SEQUENCE DESCRIPTION: SEQ ID NO:26:

Tyr Xaa Phe Phe
1

( 2 ) INFORMATION FOR SEQ ID NO:27:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 2
        ( D ) OTHER INFORMATION: /label= Tic
            / note= "1,2,3,4-tetrahydroisoquinoline-3-carboxylic acid"

( i x ) FEATURE:
        ( A ) NAME/KEY: Modified-site
        ( B ) LOCATION: 4
        ( D ) OTHER INFORMATION: /label= Phe(pNO$_2$)
            / note= "4-nitrophenylalanine"

( x i ) SEQUENCE DESCRIPTION: SEQ ID NO:27:

Tyr Xaa Trp Phe
1

( 2 ) INFORMATION FOR SEQ ID NO:28:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 2
        ( D ) OTHER INFORMATION: /label= Tic
            / note= "1,2,3,4-tetrahydroisoquinoline-3-carboxylic acid"

( i x ) FEATURE:
        ( A ) NAME/KEY: Modified-site
        ( B ) LOCATION: 4
        ( D ) OTHER INFORMATION: /note= "Trp—NH$_2$ (tryptophan amide)"

( x i ) SEQUENCE DESCRIPTION: SEQ ID NO:28:

Tyr Xaa Phe Trp
1

( 2 ) INFORMATION FOR SEQ ID NO:29:

( i ) SEQUENCE CHARACTERISTICS:
        ( A ) LENGTH: 7 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 2
        ( D ) OTHER INFORMATION: /label= Tic
            / note= "1,2,3,4-tetrahydroisoquinoline-3-carboxylic acid"

( i x ) FEATURE:
        ( A ) NAME/KEY: Modified-site
        ( B ) LOCATION: 7
        ( D ) OTHER INFORMATION: /note= "Gly—$NH_2$ (glycine amide)"

( x i ) SEQUENCE DESCRIPTION: SEQ ID NO:29:

Tyr Xaa Phe Phe Val Val Gly
1                   5

( 2 ) INFORMATION FOR SEQ ID NO:30:

( i ) SEQUENCE CHARACTERISTICS:
        ( A ) LENGTH: 7 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 2
        ( D ) OTHER INFORMATION: /label= Tic
            / note= "1,2,3,4-tetrahydroisoquinoline-3-carboxylic acid"

( i x ) FEATURE:
        ( A ) NAME/KEY: Modified-site
        ( B ) LOCATION: 7
        ( D ) OTHER INFORMATION: /note= "Ser—$NH_2$ (serine amide)"

( x i ) SEQUENCE DESCRIPTION: SEQ ID NO:30:

Tyr Xaa Phe Phe Tyr Pro Ser
1                   5

( 2 ) INFORMATION FOR SEQ ID NO:31:

( i ) SEQUENCE CHARACTERISTICS:
        ( A ) LENGTH: 7 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 2
        ( D ) OTHER INFORMATION: /label= Tic
            / note= "1,2,3,4-tetrahydroisoquinoline-3-carboxylic acid"

( i x ) FEATURE:
        ( A ) NAME/KEY: Modified-site
        ( B ) LOCATION: 7
        ( D ) OTHER INFORMATION: /note= "Ser—$NH_2$ (serine amide)"

( x i ) SEQUENCE DESCRIPTION: SEQ ID NO:31:

Tyr Xaa Trp Phe Tyr Pro Xaa
1                   5

( 2 ) INFORMATION FOR SEQ ID NO:32:

( i ) SEQUENCE CHARACTERISTICS:
        ( A ) LENGTH: 7 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 2
        ( D ) OTHER INFORMATION: /label= Tic
            / note= "1,2,3,4-tetrahydroisoquinoline-3-carboxylic acid"

( i x ) FEATURE:
        ( A ) NAME/KEY: Modified-site
        ( B ) LOCATION: 4
        ( D ) OTHER INFORMATION: /label= Phe(pNO$_2$)
            / note= "4-nitrophenylalanine"

( i x ) FEATURE:
        ( A ) NAME/KEY: Modified-site
        ( B ) LOCATION: 7
        ( D ) OTHER INFORMATION: /note= "Ser—NH$_2$ (serine amide)"

( x i ) SEQUENCE DESCRIPTION: SEQ ID NO:32:

Tyr  Xaa  Trp  Phe  Tyr  Pro  Ser
    1                           5

( 2 ) INFORMATION FOR SEQ ID NO:33:

( i ) SEQUENCE CHARACTERISTICS:
        ( A ) LENGTH: 7 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 2
        ( D ) OTHER INFORMATION: /label= Tic
            / note= "1,2,3,4-tetrahydroisoquinoline-3-carboxylic acid"

( i x ) FEATURE:
        ( A ) NAME/KEY: Modified-site
        ( B ) LOCATION: 6
        ( D ) OTHER INFORMATION: /label= Nle
            / note= "Norleucine"

( i x ) FEATURE:
        ( A ) NAME/KEY: Modified-site
        ( B ) LOCATION: 7
        ( D ) OTHER INFORMATION: /note= "Asp—NH$_2$ (aspartic acid amide)"

( x i ) SEQUENCE DESCRIPTION: SEQ ID NO:33:

Tyr  Xaa  Phe  Phe  Leu  Xaa  Asp
    1                           5

( 2 ) INFORMATION FOR SEQ ID NO:34:

( i ) SEQUENCE CHARACTERISTICS:
        ( A ) LENGTH: 5 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 3
        ( D ) OTHER INFORMATION: /label= Tic
            / note= "1,2,3,4-tetrahydroisoquinoline-3-carboxylic acid"

(ix) FEATURE:
  (A) NAME/KEY: Modified-site
  (B) LOCATION: 5
  (D) OTHER INFORMATION: /note= "Phe—NH2 (phenylalanine amide)"

(xi) SEQUENCE DESCRIPTION: SEQ ID NO:34:

Arg Tyr Xaa Phe Phe
1               5

(2) INFORMATION FOR SEQ ID NO:35:

(i) SEQUENCE CHARACTERISTICS:
    (A) LENGTH: 4 amino acids
    (B) TYPE: amino acid
    (D) TOPOLOGY: linear (ii) MOLECULE TYPE: peptide (ix) FEATURE:
    (A) NAME/KEY: Modified-site
    (B) LOCATION: 2
    (D) OTHER INFORMATION: /label= Tic
        / note= "1,2,3,4-tetrahydroisoquinoline-3-carboxylic acid"

(ix) FEATURE:
    (A) NAME/KEY: Modified-site
    (B) LOCATION: 3
    (D) OTHER INFORMATION: /label= 1- Nal
        / note= "3-(1'-naphthyl)alanine"

(xi) SEQUENCE DESCRIPTION: SEQ ID NO:35:

Tyr Xaa Ala Phe
1

δ OPIOID RECEPTOR ANTAGONISTS

THE FIELD OF THE INVENTION

This invention is related to a new class of opioid peptide analogs that are δ opioid receptor antagonists as well as to their synthesis and their use as analgesic and immunosuppressive compounds.

BACKGROUND

A known nonpeptide δ opioid antagonist is naltrindole, which is described by P. S Portoghese, et al J. Med. Chem. 31, 281–282 (1988). Naltrindole has similar δ-antagonist potency as the compounds according to this invention but is much less δ selective. Furthermore, naltrindole has also quite high μ opioid receptor affinity ($K_i^\mu$=12 nM) in the receptor binding assay and potent antagonist properties ($K_e$=29 nM) in the guinea pig ileum (GPI) assay, cf P. S. Portoghese, J. Med. Chem. 34, 1757–1762 (1991).

Another known δ-antagonist is the enkephalin analog N,N-diallyl-Tyr-Aib-Aib-Phe-Leu-OH (ICI 174864) (SEQ ID NO: 1 in the Sequence Listing) described by R. Cotton, et al. in Eur. J. Pharmacol. 97, 331–332 (1984). In comparison with the δ antagonists described in this patent application, ICI 174864 is much less δ-selective (10–300 times less) and has much lower antagonist potency in the MVD assay (40–1000 times less potent).

PRIOR ART

Tetrapeptides, which are potent δ antagonists have recently been disclosed by P. W Schiller, et al in FASEB J. 6 (No 4), A 1575 (1992), at the International Narcotics Research Conference (INRC) Meeting, Keystone, Colo., Jun. 24–29, (1992) and at the 2nd Japan Symposium on Peptide Chemistry, Shizuoka, Japan, Nov. 9–13, 1992.

THE INVENTION

It has now unexpectedly been found that the compounds of the following formula I have
- extraordinary selectivity for the δ receptor
- high potency as δ antagonists
- total lack of μ antagonist properties
- mixed μ agonist/δ antagonist properties in some cases (TIPP analogs with a C-terminal carboxamide group)

The compounds according to the present invention have the formula I

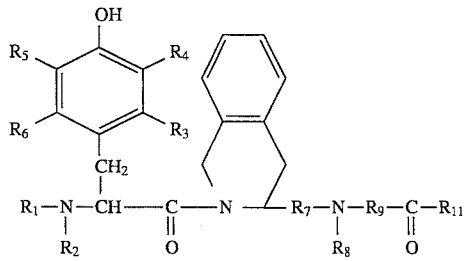

wherein $R_1$ is H, $CH_3(CH_2)_n$— wherein n=0–12—,

$CH_2$—$CH$=$CH_2$ or arginine;

$R_2$ is H, $CH_3(CH_2)_n$— wherein n=0–12—,

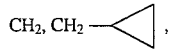

$CH_2$—$CH$=$CH_2$;

$R_3$, $R_4$, $R_5$, $R_6$ are all H or $R_4$ and $R_5$ are both H and $R_3$ and $R_6$ are both lower alkyl groups or $R_3$, $R_5$, $R_6$ are all H and $R_4$ is F, Cl, Br, OH, $NH_2$ or $NO_2$;

$R_7$ is C=O or $CH_2$;

$R_8$ is H or a lower alkyl group $R_9$ is

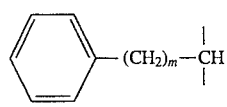

wherein m is 0–2 or

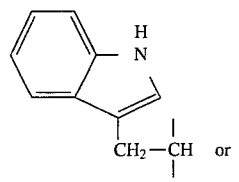

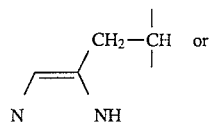

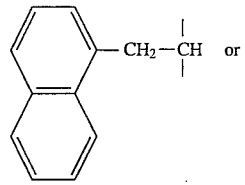

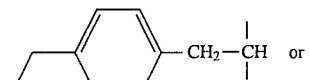

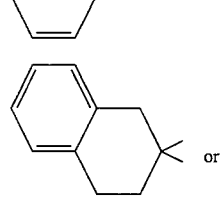

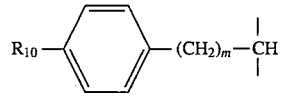

wherein $R_{10}$ is H, F, Cl, Br or I and m is 0–2;

$R_{11}$ is OH, $NH_2$ or

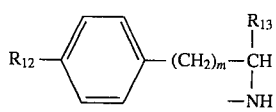

wherein $R_{12}$ is H, $NO_2$, F, Cl, Br or I, m is 0–2, $R_{13}$ is COOH, $CONH_2$, $CH_2OH$, or any additional amino acid or peptide segment, or $R_{11}$ is

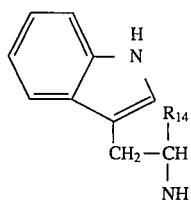

wherein $R_{14}$ is COOH, $CONH_2$, $CH_2OH$, or any additional amino acid or peptide segment;
with the exceptions of the compounds wherein $R_1$, $R_2$, $R_3$, $R_4$, $R_5$, $R_6$ and $R_8$ are all H, $R_7$ is C=O and $R_9$ is

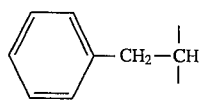

and $R_{11}$ is Phe-OH, Phe-$NH_2$, OH or $NH_2$.

A lower alkyl group has according to this specification 1–6 carbon atoms. Especially preferred compounds according to the invention are those wherein $R_7$ is $CH_2$ (as part of a reduced peptide bond). A reduced peptide bond gives the compound higher δ antagonist potency, increased δ-selectivity, better stability in organic solvents and resistance to enzymatic degradation.

Further preferred compounds according to the invention are those, wherein $R_4$ and $R_5$ are H and $R_3$ and $R_6$ are both methyl groups.

Synthesis

Most Boc-amino acid derivatives used in the peptide syntheses were commercially available. 2,6-dimethyl-tyrosine (Dmt) was prepared as described by J. H Dygos et al. Synthesis, No 8 (August) pp. 741–743 (1992) and 2-aminotetralin 2-carboxylic acid as described by P. W. Schiller et al in J. Med. Chem 34, 3125–3132 (1991).

All peptides were prepared by solid-phase techniques. The usual polystyrene/divinylbenzene resin was used for the solid-phase synthesis of peptides with a free C-terminal carboxyl group, whereas peptide amides were synthesized by using the p-methylbenzhydrylamine resin. Boc protection of the amino group was employed in the preparation of all peptides. The syntheses were performed according to protocols that have been extensively used in the inventor's laboratory (P. W Schiller et al, Biochemisty 16, 1831–1832 (1977)). Couplings were performed in $CH_2Cl_2$ or DMF, using dicyclohexylcarbodiimide/1-hydroxybenzotriazole (DCC/HOBt) as coupling agents. Completeness of coupling was carefully examined after each coupling step by means of the ninhydrin color test. The fully assembled peptide chain was cleaved from the resin and completely deprotected by treatment with liquid HF at 0° C. and in the presence of anisole as scavenger (60–90 min).

Analogs containing the $CH_2NH$ peptide bond isostere were prepared by solid-phase synthesis according to a procedure developed by Sasaki and Coy (Y. Sasaki & D. H. Coy, Peptides 8, 119–121 (1987)). With this method the $CH_2NH$ peptide bond can be directly introduced by the reductive alkylation reaction between a Boc-amino acid aldehyde and an amino group on the resin-bound peptide employing sodium cyanoborohydride in acidified DMF. No significant racemization was observed with this method. Boc-Tic aldehyde was synthesized via the corresponding Boc-Tic N-methoxy-N-methylamide by the reportedly racemization-free $LiAlH_4$ reduction method (J. A Fehrentz & B. Castro, Synthesis, 676–678 (1983)). Peptides containing reduced peptide bonds were cleaved from the resin and deprotected by treatment with HF/anisole as described above.

Crude products obtained from solid-phase peptide synthesis required extensive purification by various chromatographic techniques or by other methods. Following HF cleavage and extraction of the resin, gel filtration on Sephadex (G-15 or G-25) was routinely performed. Various subsequent purification steps included partition chromatography on Sephadex G-25 (using various butanol-acetic acid-pyridine-water two phase systems), ion exchange chromatography (DEAE-Sephadex, SP-Sephadex and CM-cellulose) and reversed-phase chromatography on an octadecasilyl-silica column using linear gradients of methanol in 1% trifluoroacetic acid (low pressure). If necessary, final purification to homogeneity was performed by semi-preparative HPLC. Semi-preparative μ-Bondapak C-18 columns (Waters; 0.7×25 cm), which, depending on the separation problem, permitted purification of 2–20 mg peptide material per run were used. Several highly sensitive and efficient analytical methods were used to demonstrate homogeneity of the prepared peptides and to verify their structures. Thin layer chromatography in at least two different solvent systems was used to establish purity. Furthermore, analytical HPLC in two or three different solvent systems was routinely used in the laboratory as a highly sensitive purity test. Verification of peptide structures was mainly based on amino acid analysis and fast atom bombardment-mass spectrometry (FAB-MS). For amino acid analyses, peptides were hydrolyzed in 6N HCl containing a small amount of phenol for 24 h at 110° C. in deaerated tubes (in some case hydrolyses lasting for 12 and 48 h were also performed to take into account amino acid degradation). Hydrolysates were analyzed on a Beckman Model 121 Camino acid analyzer equipped with a system AA computing integrator. FAB mass spectrometry was used to establish the correct molecular weights of the peptides.

EXAMPLES OF PARTICULAR ANALOGS

EXAMPLE 1

H-Tyr-Tic-Hfe-Phe-OH (SEQ ID NO: 2 in the Sequence listing)

Boc-Phe-O-resin (1 g, 0.61 mmol Boc-Phe/g resin; Peninsula, Belmont, Calif.) was washed with reagents in the following sequence: $CH_2Cl_2$ (3×1 min), 50% (v/v) TFA in $CH_2Cl_2$ (30 min), $CH_2Cl_2$ (5×1 min), 10% (v/v) DIEA in $CH_2Cl_2$ (2×5 min), $CH_2Cl_2$ (5×1 min). Boc-Hfe-OH (425 mg, 1.52 mmol) was then coupled using HOBt (205 mg, 1.52 mmol) and DCC (313 mg, 1.52 mmol) in CH$_2$Cl$_2$/DMF (3:1, v/v) for 17 h. The resin was then washed with CH$_2$Cl$_2$ (3×1 min), EtOH (1 min), CH$_2$Cl$_2$ (3×1 min). This sequence of washes and reactions was repeated for the addition of each of the residues with the following modifications.

After coupling of Boc-Tic-OH the resin was washed with CH$_2$Cl$_2$/DMF (3:1, v/v) (3×) and a recoupling step using the same amounts of Boc-Tic-OH, HOBt and DCC in CH$_2$Cl$_2$/DMF (3:1, v/v) was performed for another 17h. The same recoupling step was also carried out to couple Boc-Tyr-(Boc)-OH. After final deprotection with 50% (v/v) TFA in CH$_2$Cl$_2$ (30 min), the resin was washed with CH$_2$Cl$_2$ (3×1 min) and EtOH (3×1 min) and was dried in a desiccator. The dry resin was treated with 20 ml of HF plus 1 ml of anisole first for 90 min at 0° C. and then for 15 min at room temperature. After evaporation of the HF, the resin was extracted three times with Et$_2$O and, subsequently three times with 7% AcOH. The crude peptide was then obtained in solid form through lyophilization of the combined acetic acid extracts.

The peptide was purified by gel filtration on a Sephadex-G-25 column in 0.5N AcOH followed by reversed-phase chromatography on an octadecasilyl silica column with a linear gradient of 0–80% MeOH in 1% TFA. After solvent evaporation the pure peptide was dissolved in conc. AcOH and was obtained in solid form through lyophilization.

Yield: 45 mg

FAB-MS:MH$^+$=648

TLC (silica) Rf 0.75 n-BuOH/AcOH/H$_2$O (4/1/5, organic phase) Rf 0.70 n-BuOH/Pyridine/AcOH/H$_2$O (15/10/3/12)

Amino acid analysis: Tyr 0.96, Hfe 1.03, Phe 1.00

EXAMPLE 2

H-Tyr-TicΨ[CH$_2$—NH]Phe-Phe-OH (SEQ ID NO: 3 in the Sequence Listing)

The synthesis of this peptide was performed as in the case of EXAMPLE 1 using the same resin, except that the introduction of a reduced peptide bond between the Tic$^2$ and Phe$^3$ residue required a reductive alkylation reaction between Boc-Tic aldehyde and the amino group of the resin-bound H-Phe-Phe dipeptide.

Preparation of
N-t-butoxycarbonyl-L-1,2,3,4-tetrahydroisoquinoline-3-aldehyde (Boc-Tic aldehyde) via
N-t-butoxycarbonyl-L-1,2,3,4-tetrahydroisoquinoline-3-N-methoxy, N-methylamide.

BOP (benzotriazol-1-yl-oxytris(dimethylamino]phosphonium hexafluorophosphate) (3.48 g, 10 mmol) was added to a stirred solution of Boc-Tic-OH (2.8 g, 10 mmol) and triethylamine (1.33 ml, 10 mmol) in CH$_2$Cl$_2$. After five minutes, N-dimethylhydroxylamine hydrochloride (1.2 g, 12 mmol) and triethylamine (1.68 ml, 12 mmol) were added to the solution. The reaction was carried out for 17h. Subsequently, the reaction mixture was diluted with dichloromethane and washed with 3N HCl, a saturated aqueous solution of NaHCO$_3$ and a saturated aqueous solution of NaCl. The organic solution was dried over MgSO$_4$ prior to evaporation of the solvent. The resulting crude product of N-t-butoxycarbonyl-L-1,2,3,4-tetrahydroisoquinoline-3-N-methoxy, N-methylamide was purified by chromatography on a silica gel column in EtOAc/hexane(1:2, v/v).

Yield: 2.1 g (65%), oil

TLC (silica) Rf 0.57 EtOAc/hexane (1/1) Rf 0.30 EtOAc/hexane (1/2)

NMR (CDCl$_3$) δ 1.45 (9H, t-butyl), 3.00 (2H,H-4), 3.18 (3H, NCH$_3$), 3.8(3H, OCH$_3$), 4.42–4.90(3H, 2H-I and 1H-3), 7.17(4H, ar)

To a stirred solution of N-t-butoxycarbonyl-L-1,2,3,4-tetrahydroisoquinoline-3-N-methoxy, N-methyamide (1.2 g, 4mmol) in 30 ml ether 190 mg (5 mmol) of lithium aluminium hydride were added. The reduction reaction was carried out for 1 h and the reaction mixture was then hydrolyzed with a solution of KHSO$_4$ (954 mg, 7 mmol) in water (20 ml). Subsequently, the aqueous phase was separated and extracted with three 50 ml portions of ether. The four organic phases were combined, washed with 3N HCl, a saturated aqueous solution of NaHCO$_3$ and a saturated aqueous solution of NaCl, and finally dried over MgSO$_4$. After solvent evaporation the aldehyde was obtained in pure form as an oil.

Yield: 635 mg (60%), oil

TLC (silica) Rf 0.84 EtOAc/hexane (1/1) Rf 0.57 EtOAc/hexane (1/2)

NMR(CDCl$_3$) δ 1.5 (9H, t-butyl), 3.0–3.27 (2H, H-4), 4.4–4.8 (3H, 1H-3 and 2H-1), 7.0–7.2 (4H, ar), 9,43 (1H, CHO)

Reductive Alkylation Reaction between Boc-Tic Aldehyde and the H-Phe-Phe-O Resin The resin was washed with DMF (2×1 min) and then Boc-Tic aldehyde (392 mg, 1.52 mmol) in DMF containing 1% AcOH was added to the resin. Sodium cyanoborohydride (115 mg, 1.83 mmol) was then added portionwise over a period of 40 min and the reaction was allowed to continue for 3h.

After coupling of the N-terminal tyrosine residue and deprotection the peptide was cleaved from the resin, purified and lyophilized as described in EXAMPLE 1.

Yield: 180 mg

FAB-MS: MH$^+$=633

TLC (silica) Rf 0.73 n-BuOH/AcOH/H$_2$O (4/1/5, organic phase) Rf 0.69 n-BuOH/pyridine/AcOH/H$_2$O (15/10/3/12)

Amino acid analysis: Tyr 0.95, Phe 1.00

The following compounds according to the invention have been synthesized and tested as δ antagonists.

Pharmacological Testing In Vitro of δ Opioid Antagonists a) Biosassys based on inhibition of electrically evoked contractions of the mouse vas deferens (MVD) and of the guinea pig ileum (GPI). In the GPI assay the opioid effect is primarily mediated by μ opioid receptors, whereas in the MVD assay the inhibition of the contractions is mostly due to interaction with δ opioid receptors. Antagonist potencies in these assays are expressed as so-called K$_e$-values (H. W. Kosterlitz & A. J. Watt, Br. J. Pharmacol. 33, 266–276 (1968)). Agonist potencies are expressed as IC50 values (concentration of the agonist that produces 50% inhibition of the electrically induced contractions).

Bioassays Using Isolated Organ Preparations

The GPI and MVD bioassays were carded out as reported in P. W. Schiller et al., Biochem. Biophys. Res. Commun 85, 1332–1338 (1978) and J. Di Maio et al., J. Med. Chem. 25, 1432–1438 (1982). A log dose-response curve was determind with [Leu⁵]enkephalin as standard for each ileum and vas preparation, and IC50 values of the compounds being tested were normalized according to A. A Waterfield et al., Eur. J. Pharmacol. 58, 11–18 (1979). $K_e$ values for the TIPP-related antagonists were determind from the ratio of IC50 values (DR) obtained in the presence and absence of a fixed antagonist concentration (a) ($K_e$=a/(DR-1)) H. W. Kosterlitz & A. J. Watt, Br. J. Pharmacol. 33, 266–276 (1968). These determinations were made with the MVD assay, using three different δ-selective agonists ([Leu⁵] enkephalin, DPDPE and [D-Ala²]deltorphin I].

In the following Table 1 the results are given.

Specific embodiments of the invention which have four or more amino acids and which are also listed in Table 1 are identified in the Sequence Listing as follows:

H-Tyr-Tic-Phe-Phe-OH (SEQ ID NO: 4);
H-Tyr-Tic-Phe-Phe-NH₂ (SEQ ID NO: 5);
Tyr(NᵅMe)-Tic-Phe-Phe-OH (SEQ ID NO: 6);
Tyr(NᵅCpm)-Tic-Phe-Phe-OH (SEQ ID NO: 7);
Tyr(NᵅHex)-Tic-Phe-Phe-OH (SEQ ID NO: 8);
Tyr(NᵅEt₂)-Tic-Phe-Phe-OH (SEQ ID NO: 9);
H-Dmt-Tic-Phe-Phe-OH (SEQ ID NO: 10);
H-Dmt-Tic-Phe-Phe-NH₂ (SEQ ID NO: 11);
H-Tyr(3-F)-Tic-Phe-Phe-OH (SEQ ID NO: 12);
H-Tyr(3-Cl)-Tic-Phe-Phe-OH (SEQ ID NO: 13);
H-Tyr(3-Br)-Tic-Phe-Phe-OH (SEQ ID NO: 14);
H-Dmt-TicΨ[CH₂—NH]Phe-Phe-OH (SEQ ID NO: 15);
H-Dmt-TicΨ[CH₂—NH]Phe-Phe-NH₂ (SEQ ID NO: 16);
H-Tyr-TicΨ[CH₂—NCH₃]Phe-Phe-OH (SEQ ID NO: 17);
H-Tyr-Tic-Ψ[CH₂—NH]Hfe-Phe-OH (SEQ ID NO: 18);
Tyr(NMe)-TicΨ[CH₂—NH]Hfe-Phe-OH (SEQ ID NO: 19);
H-Tyr-Tic-Phg-Phe-OH (SEQ ID NO: 20);
H-Tyr-Tic-Trp-Phe-OH (SEQ ID NO: 21);
H-Tyr-Tic-Trp-Phe-NH₂ (SEQ ID NO: 22);
H-Tyr-Tic-His-Phe-OH (SEQ ID NO: 23);
H-Tyr-Tic-2-Nal-Phe-OH (SEQ ID NO: 24);
H-Tyr-Tic-Atc-Phe-OH (SEQ ID NO: 25);
H-Tyr-Tic-Phe-Phe(pNO₂)-OH (SEQ ID NO: 26);
H-Tyr-Tic-Trp-Phe(pNO₂)-OH (SEQ ID NO: 27);
H-Tyr-Tic-Phe-Trp-NH₂ (SEQ ID NO: 28);
H-Tyr-Tic-Phe-Phe-Val-Val-Gly-NH₂ (SEQ ID NO: 29);
H-Tyr-Tic-Phe-Phe-Tyr-Pro-Ser-NH₂ (SEQ ID NO: 30);
H-Tyr-Tic-Trp-Phe-Tyr-Pro-Ser-NH₂ (SEQ ID NO: 31);
H-Tyr-Tic-Trp-Phe (pNO₂)-Tyr-Pro-Ser-NH₂ (SEQ ID NO: 32) and
H-Tyr-Tic-Phe-Phe-Leu-Nle-Asp-NH₂ (SEQ ID NO: 33).

TABLE 1

$K_e$-values of TIP(P) related peptides in the MVD assay
(Antagonist potencies against the δ agonists [Leu5] enkephalin,
[D-Pen², D-Pen⁵]enkephalin (DPDPE) and [D-Ala²]deltorphin I)
(Prior known compounds are marked (P))

| Compound | $K_e$ (nM)ᵃ | | |
|---|---|---|---|
| | [Leu⁵] Enkephalin | DPDPE | [D-Ala²] deltorphin I |
| H—Tyr—Tic—Phe—Phe—OH(P)(TIPP) | 5.86 ± 0.33 | 4.80 ± 0.20 | 2.96 ± 0.02 |
| H—Tyr—Tic—Phe—Phe—NH₂(P)(TIPP—NH₂)ᵇ | 15.7 ± 2.4 | 18.0 ± 2.0 | 14.4 ± 2.2 |
| H—Tyr—Tic—Phe—OH(P)(TIP) | 11.7 ± 1.8 | 16.1 ± 1.9 | 12.6 ± 1.8 |
| H—Tyr—Tic—Phe—NH₂(P)(TIP—NH₂) | 43.9 ± 8.9 | 96.8 ± 14.1 | 58.9 ± 7.7 |
| Tyr(NᵅMe)-Tic—Phe—Phe—OH | 1.01 ± 0.15 | 1.22 ± 0.17 | 0.436 ± 0.071 |
| Tyr(NᵅCpm)-Tic—Phe—Phe—OH | 29.6 ± 4.4 | 28.2 ± 0.5 | 32.5 ± 1.3 |
| Tyr(NᵅHex)-Tic—Phe—Phe—OH | 9.37 ± 1.18 | 4.28 ± 0.56 | 10.6 ± 1.9 |
| Tyr(NᵅEt₂)-Tic—Phe—Phe—OH | 3.39 ± 0.16 | 0.893 ± 0.112 | 2.30 ± 0.18 |
| H—Dmt—Tic—Phe—Phe—OH | 0.169 ± 0.015 | 0.196 ± 0.022 | 0.130 ± 0.017 |
| H—Dmt—Tic—Phe—Phe—NH₂ᵇ | 0.221 ± 0.028 | 0.209 ± 0.037 | 0.260 ± 0.064 |
| H—Tyr(3-F)—Tic—Phe—Phe—OH | 5.88 ± 0.72 | 13.0 ± 0.7 | 8.73 ± 1.21 |
| H—Tyr(3-Cl)—Tic—Phe—Phe—OH | 18.0 ± 2.2 | 20.4 ± 1.5 | 19.9 ± 1.7 |
| H—Tyr(3-Br)—Tic—Phe—Phe—OH | 18.2 ± 2.7 | 31.3 ± 4.2 | 23.9 ± 2.7 |
| H—Tyr—Tic-ψ[CH₂—NH]Phe—OH | 9.12 ± 1.57 | 9.06 ± 0.70 | 8.24 ± 1.12 |
| H—Tyr—Tic-ψ[CH₂—NH]Phe—Phe—OH | 2.46 ± 0.35 | 2.89 ± 0.23 | 2.85 ± 0.13 |
| H—Dmt—Ticψ[CH₂— | 0.259 ± 0.043 | 0.196 ± 0.033 | 0.157 ± 0.028 |

TABLE 1-continued $K_e$-values of TIP(P) related peptides in the MVD assay
(Antagonist potencies against the δ agonists [Leu5] enkephalin,
[D-Pen$^2$, D-Pen$^5$]enkephalin (DPDPE) and [D-Ala$^2$]deltorphin I)
(Prior known compounds are marked (P))

| | $K_e$ (nM)$^a$ | | |
|---|---|---|---|
| Compound | [Leu$^5$] Enkephalin | DPDPE | [D-Ala$^2$] deltorphin I |
| H — Dmt — Ticψ[CH$_2$ — NH]Phe — Phe — OH | | | |
| H — Dmt — Ticψ[CH$_2$ — NH]Phe — Phe — NH$_2$$^b$ | 0.470 ± 0.078 | 0.420 ± 0.049 | 0.486 ± 0.058 |
| H — Tyr — Ticψ[CH$_2$ — NCH$_3$]Phe — Phe — OH | 6.28 ± 0.14 | 4.76 ± 0.48 | 2.89 ± 0.31 |
| H — Tyr — Ticψ[CH$_2$ — NH]Hfe — Phe — OH | 2.22 ± 0.31 | 2.64 ± 0.47 | 1.90 ± 0.17 |
| H — Tyr — Tic — Hfe — Phe — OH | 1.23 ± 0.18 | 0.609 ± 0.043 | 0.408 ± 0.039 |
| Tyr(NMe)-Ticψ[CH$_2$ — NH]Hfe — Phe — OH | 0.780 ± 0.082 | 0.902 ± 0.135 | 0.418 ± 0.098 |
| H — Tyr — Tic — Phg — Phe — OH | 13.8 ± 1.2 | 21.5 ± 2.9 | 8.31 ± 1.75 |
| H — Tyr — Tic — Trp — OH | 10.6 ± 2.1 | 6.23 ± 0.79 | 5.36 ± 0.77 |
| H — Tyr — Tic — Trp — Phe — OH(P) | 2.37 ± 0.54 | 2.56 ± 0.21 | 1.65 ± 0.18 |
| H — Tyr — Tic — Trp — Phe — NH$_2$(P) | 3.24 ± 0.43 | 4.65 ± 0.92 | 2.31 ± 0.17 |
| H — Tyr — Tic — His — Phe — OH | 20.1 ± 1.8 | 18.2 ± 1.6 | 18.7 ± 0.7 |
| H — Tyr — Tic-2-Nal — Phe — OH | 2.64 ± 0.17 | 4.41 ± 0.65 | 4.17 ± 0.58 |
| H — Tyr — Tic — Atc — Phe — OH | 1.63 ± 0.14 | 1.85 ± 0.16 | 0.927 ± 0.142 |
| H — Tyr — Tic — Phe — Phe(pNO$_2$) — OH | 3.62 ± 0.46 | 3.30 ± 0.35 | 2.79 ± 0.46 |
| H — Tyr — Tic — Trp — Phe(pNO$_2$) — OH | 1.83 ± 0.10 | 4.40 ± 0.55 | 2.27 ± 0.14 |
| H — Tyr — Tic — Phe — Trp — NH$_2$ | 49.5 ± 4.6 | 41.3 ± 5.2 | 38.6 ± 3.3 |
| H — Tyr — Tic — Phe — Phe — Val — Val — Gly — NH$_2$ | 6.48 ± 0.59 | 6.36 ± 1.32 | 4.96 ± 0.77 |
| H — Tyr — Tic — Phe — Phe — Tyr — Pro — Ser — NH$_2$ | 4.78 ± 0.80 | 4.63 ± 0.43 | 3.90 ± 0.63 |
| H — Tyr — Tic — Trp — Phe — Tyr — Pro — Ser — NH$_2$ | 4.20 ± 1.13 | 3.65 ± 0.94 | 3.65 ± 0.14 |
| H — Tyr — Tic — Trp — Phe(pNO$_2$) — Tyr — Pro — Ser — NH$_2$ | 3.68 ± 0.79 | 2.48 ± 0.34 | 3.91 ± 0.38 |
| H — Tyr — Tic — Phe — Phe — Leu — Nle — Asp — NH$_2$ | 21.4 ± 1.0 | 10.4 ± 2.3 | 10.8 ± 3.1 |
| Naltrindole(P) | 0.850 ± 0.221 | 0.632 ± 0.161 | 0.636 ± 0.105 |

$^a$Values are means of 3–8 determinations ± SEM
$^b$H — Tyr — Tic — Phe — Phe — NH$_2$, H — Dmt — Tic — Phe — Phe — NH$_2$ and H — Dmt — Ticψ[CH$_2$ — NH]Phe — Phe — NH$_2$ are mixed μ agonist/δ antagonists showing IC50s of 1700 ± 220 nM, 18.2 ± 1.8 nM and 7.71 ± 0.32 nM, respectively, in the guinea pig ileum (GPI) assay.

Conclusion

μ Antagonist or μ Agonist Behavior of TIPP-Related δ Antagonists

All compounds show no μ antagonist activity in the GPI assay at concentrations as high as 10 μM.

TIPP-related peptides with a free C-terminal carboxyl group have very weak μ agonist potency in the GPI assay (IC50>10 μM). On the other hand, TIPP-derived peptides with a C-terminal carboxamide function show full μ agonist potency in the GPI assay (e.g. H-Dmt-Tic-Phe-Phe-NH$_2$) has an IC50 of 18.2±1.8 nM in the GPI assay.

Opioid Receptor Binding Assays

μ and δ opioid receptor binding constants ($K_i^\mu$, $K_i^\delta$) of the compounds were determined by displacement of relatively selective μ and δ radioligands from binding sites in rat brain membrane preparations (calculated from the measured IC50 values on the basis of the equation by Cheng & Prusoff (Y. C. Cheng and W. H. Prusoff (Biochem. Pharmacol. 22, 3099–3102 (1973)).

In the follwing Table 2 the results of opioid receptor binding assays are given. The ratio $K_i^\mu/K_i^\delta$ is a quantitative measure of the δ-selectivity. The higher the ratio the better the δ-selectivity.

Opioid Receptor Binding Studies

The μ-, δ- and κ-opioid receptor affinities of all new analogs were determined in binding assays based on displacement of μ-, δ- and κ-selective radioligands from rat brain membrane binding sites. In the case of κ-ligands guinea pig brain homogenates were used, since the relative proportion of κ-binding sites is higher in guinea pig brain than in rat brain. The experimental procedure being used in our laboratory represents a modified version of the binding assay described by Pasternak et al. (Mol. Pharmacol. 11, 340–351, (1975)). Male Sprague-Dawley rats (300–350 g) from the Canadian Breeding Laboratories were decapitated and after removal of the cerebellum the brains were homogenized in 30 volumes of ice-cold standard buffer (50 mM Tris-HCl, pH 7.7). After centrifugation at 30,000×g for 30 min at 4° C. the membranes were reconstituted in the original volume of standard buffer and incubated for 30 min at 37° C. (to realease bound endogenous ligands). Subsequent centrifugation and resuspension of the pellet in the initial volume of fresh standard buffer yielded the final membrane suspension. Aliquots (2 ml) of the membrane preparations were incubated for 1–2 h at 25° C. with 1 ml standard buffer containing the peptide to be tested and one of the following radioligands at the final concentration indicated: [$^3$H]DAMGO, μ-selective, 0.7 nM; [$^3$H]DSLET, [$^3$H]DPDPE, or [$^3$H]TIPP, δ-selective, 1.0 nM; and [$^3$H] U69,563, κ-selective, 0.5 nM. The incubation was terminated by filtration through Batman GF/B filters under vacuum at 4° C. Following two washings with 5 ml portions of ice-cold standard buffer the filters were transferred to scintillation vials and treated with 1 ml Protosol (New England Nuclear) for 30 min prior to the addition of 0.5 ml acetic acid and 10 ml Aquasol (New England Nuclear). After shaking for 30 min the vials were counted at an efficiency of 40–45%. All experiments were performed in duplicates and repeated at least three times. Specific binding of each of the three radioligands was defined by performing incubations in the presence of cold DAMGO, DSLET and U69,563, respectively, at a concentration of 1 micromolar. Values of half-maximal inhibition (IC50) of specific binding were obtained graphically from semilogarithmic plots. From the measured IC50-values, binding inhibition constants ($K_i$) were then calculated based on Cheng and Prusoff's equation (Biochem, Pharmacol. 22, 3099–3102 (1973)). Ratios of the $K_i$-values in the μ-, δ- and κ-representative binding assays are a measure of the receptor selectivety of the compound under investigation (e.g. $K_i^\mu/K_i^\delta$ indicates the selectivity for δ-receptors versus μ-receptors). None of the compounds according to the claimed invention had significant affinity for κ-receptors.

Specific embodiments of the invention which have four amino acids or more and which are also listed in Table 2 are identified in the Sequence Listing as follows: H-Arg-Tyr-Tic-Phe-Phe-NH$_2$ (SEQ ID NO: 34) and H-Tyr-Tic-1-Nal-Phe-OH (SEQ ID NO: 35).

TABLE 2

Receptor binding data of opioid peptide analogs[a]

| Compound | $K_i^\mu$ [nM] | $K_i^\delta$ [nM] | $K_i^\mu/K_i^\delta$ |
|---|---|---|---|
| H—Tyr—Tic—Phe—Phe—OH(P)(TIPP) | 1720 ± 50 | 1.22 ± 0.07 | 1410 |
| H—Tyr—Tic—Phe—Phe—NH$_2$(P)(TIPP-NH$_2$) | 78.8 ± 7.1 | 3.00 ± 0.15 | 26.3 |
| H—Tyr—Tic—Phe—OH(P)(TIP) | 1280 ± 140 | 9.07 ± 1.02 | 141 |
| H—Tyr—Tic—Phe—NH$_2$(P)(TP-NH$_2$) | 624 ± 79 | 12.0 ± 1.3 | 52.0 |
| Tyr(N$^\alpha$Me)-Tic—Phe—Phe—OH | 13400 ± 600 | 1.29 ± 0.36 | 10400 |
| Tyr(N-Hex)-Tic—Phe—Phe—OH | 1080 ± 80 | 0.951 ± 0.123 | 1140 |
| H—Dmt—Tic—Phe—Phe—OH | 141 ± 0.24 | 0.248 ± 0.046 | 569 |
| H—Dmt—Tic—Phe—Phe—NH$_2$ | 1.19 ± 0.11 | 0.118 ± 0.016 | 10.1 |
| H—Arg—Tyr—Tic—Phe—Phe—NH$_2$ | 107 ± 2 | 4.79 ± 0.15 | 22.3 |
| H—Tyr—TicΨ[CH$_2$—NH]Phe—OH | 10800 ± 1300 | 1.94 ± 0.14 | 5570 |
| H—Tyr—TicΨ[CH$_2$—NH]Phe—Phe—OH | 3228 ± 439 | 0.308 ± 0.060 | 10500 |
| H—Dmt—TicΨ[CH$_2$—NH]Phe—Phe—OH | 95.5 ± 11.0 | 1.70 ± 0.40 | 56.2 |
| H—Tyr—TicΨ[CH$_2$—NCH$_3$]Phe—Phe—OH | 13400 ± 700 | 0.842 ± 0.116 | 15900 |
| H—Tyr—Tic—Hfe—Phe—OH | 1990 ± 170 | 0.277 ± 0.001 | 7180 |
| H—Tyr—Tic—Phg—Phe—OH | 29000 ± 7200 | 3.01 ± 0.54 | 9630 |
| H—Tyr—Tic—Trp—Phe—NH$_2$(P) | 176 ± 21 | 0.248 ± 0.009 | 709 |
| H—Tyr—Tic—Trp—Phe—OH(P) | 1790 ± 380 | 0.301 ± 0.042 | 5950 |
| H—Tyr—Tic—His—Phe—OH | 17000 ± 3700 | 1.48 ± 0.22 | 11500 |
| H—Tyr—Tic-1-Nal—Phe—OH | 1120 ± 130 | 1.14 ± 0.17 | 982 |
| H—Tyr—Tic-2-Nal—Phe—OH | 6330 ± 130 | 1.31 ± 0.03 | 4830 |
| H—Tyr—Tic—Phe—Phe(pNO$_2$)—OH(P) | 2890 ± 660 | 0.703 ± 0.099 | 4110 |
| H—Tyr—Tic—Trp—Phe(pNO$_2$)—OH(P) | 1520 ± 42 | 0.330 ± 0.004 | 4610 |
| H—Tyr—Tic—Phe—Trp—NH$_2$(P) | 312 ± 75 | 1.21 ± 0.19 | 258 |
| H—Tyr—Tic—Phe—Phe—Val—Val—Gly—NH$_2$ | 3290 ± 520 | 1.43 ± 0.25 | 2300 |
| H—Tyr—Tic—Phe—Phe—Tyr—Pro—Ser—NH$_2$ | 658 ± 136 | 0.900 ± 0.196 | 731 |
| Naltrindole | 12.2 ± 1.9 | 0.687 ± 0.100 | 17.8 |

[a]Values are means of 3 determinations ± SEM

Potential Use

The pure δ antagonists may be used in combination with analgesics of the μ agonist type (e.g. morphine) to prevent the development of tolerance and dependence, as suggested by the results of E. E. Abdelhamid et al., J. Parmacol. Exp. Ther. 258, 299–303 (1991). The latter study also suggested that compounds with mixed μ agonist/δ antagonist properties may be therapeutically useful as analgesics that do not produce tolerance and dependence. The TIPP-related peptides with a C-terminal carboxamide group described in this patent are the first mixed μ agonist/δ antagonists known.

The δ antagonists described in the patent may also be therapeutically useful as immunosuppressive agents. Immunosuppressive effects of the less δ-selective and less "pure" δ antagonist naltrindole have been described by K. Arakawa et al. Transplantation Proc. 24, 696–697 (1992); Transplantation 53, 951–953 (1992).

Abbreviations

Aib=α-aminoisobutyric acid
Atc=2-aminotetralin-2-carboxylic acid
Boc=tert-butoxycarbonyl
Cpm=cyclopropylmethyl
DAMGO=H-Tyr-D-Ala-Gly-Phe(N$^\alpha$Me)-Gly-ol
DCC=dicyclohexylcarbodiimide
DIEA=diisopropylethylamine
Dmt=2,6-dimethyltyrosine DPDPE = [D-Pen$^2$, D-Pen$^5$]enkephalin (cyclic)

DSLET=H-Tyr-D-Ser-Gly-Phe-Leu-Thr-OH
Et=ethyl
FAB-MS=fast atom bombardment mass spectrometry
GPI=guinea pig ileum
Hex=hexyl
Hfe=homophenylalanine
HOBt=1-hydroxybenzotriazole
MVD=mouse vas deferens
1-Nal=3-(1'-naphthyl)alanine
2-Nal=3-(2'-naphthyl)alanine
Phe(pNO$_2$)=4-nitrophenylalanine
Phg=phenylglycine
Tic=1,2,3,4-tetrahydroisoquinoline-3-carboxylic acid
TIP=H-Tyr-Tic-Phe-OH
TIP-NH$_2$=H-Tyr-Tic-Phe-NH$_2$
TIP(Ψ)=H-Tyr-TicΨ[CH$_2$-NH]Phe-OH
TIPP=H-Tyr-Tic-Phe-Phe-OH
TIPP-NH$_2$=H-Tyr-Tic-Phe-Phe-NH$_2$
TIPP(Ψ)=H-Tyr-TicΨ[CH$_2$-NH]Phe-Phe-OH
Tyr(3-Br)=3-bromotyrosine
Tyr(3-Cl)=3-chlorotyrosine
Tyr(3-F)=3-fluorotyrosine
Tyr(N$^\alpha$Me)=N$^\alpha$-methyltyrosine
U69,593=(5α, 7α, 8β)-(−)-N-methyl-[7-(1-pyrrolidinyl)-1-oxaspiro[4,5]dec-8yl]benzeneacetamide

---

I claim:
1. A compound of the formula I

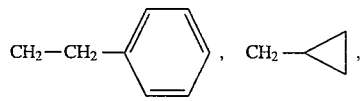

wherein
$R_1$ is H, $CH_3(CH_2)_n—$ wherein n=0–12,

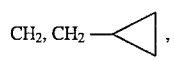

$CH_2—CH=CH_2$ or arginine;
$R_2$ is H, $CH_3(CH_2)_n—$ wherein n=0–12, $CH_2, CH_2—\triangleleft$, or $CH_2—CH=CH_2$;
$R_3$, $R_4$, $R_5$, $R_6$ are all H or
$R_4$ and $R_5$ are both H and $R_3$ and $R_6$ are both lower alkyl groups or $R_3$, $R_5$, $R_6$ are all H and $R_4$ is F, Cl, Br, OH, $NH_2$ or $NO_2$;
$R_7$ is C=O or $CH_2$;

$R_8$ is H or a lower alkyl group;
$R_9$ is

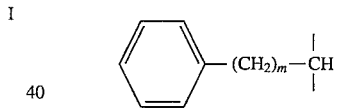

wherein m is 0–2 or

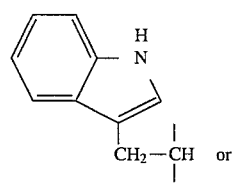

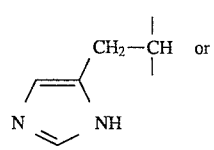

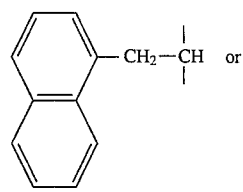

-continued

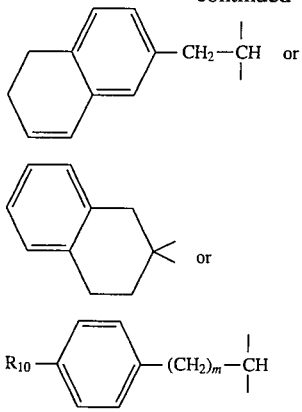

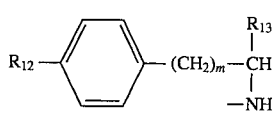

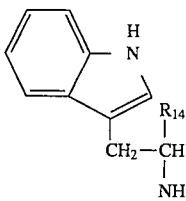

wherein $R_{10}$ is H, F, Cl, Br or I and m is 0–2;

$R_{11}$ is OH, $NH_2$ or $R_{12}$—⬡—$(CH_2)_m$—CH($R_{13}$)—NH wherein $R_{12}$ is H, $NO_2$, F, Cl, Br or I, m is 0–2;

$R_{13}$ is —COOH, —$CONH_2$, —$CH_2OH$, or —CO—X, wherein X is an amino acid, or a peptide of 2–7 amino acids; or $R_{11}$ is

[indole structure with $CH_2$—CH($R_{14}$)—NH]

wherein $R_{14}$ is COOH, $CONH_2$, $CH_2OH$, or —CO—X, wherein X is an amino acid, or a peptide of 2–7 amino acids;

with the exception of the compounds Tyr-Tic-Phe-OH, Tyr-Tic-Phe-$NH_2$, Tyr-Tic-Phe-Phe-OH, Tyr-Tic-Phe-Phe-$NH_2$, Tyr-Tic-Trp-Phe-$NH_2$, Tyr-Tic-Trp-Phe-OH, Tyr-Tic-Phe-Phe(P-$NO_2$)-OH, Tyr-Tic-Trp-Phe(p-$NO_2$)-OH, Tyr-Tic-Phe-Trp-$NH_2$, and Tyr-Tic-Phe-Phe-Leu-Nle-Asp-$NH_2$.

2. A compound according to formula I of claim 1, wherein $R_7$ is $CH_2$.

3. A compound according to formula I of claim 1, wherein $R_4$ and $R_5$ are hydrogen and $R_3$ and $R_6$ are both methyl groups.

4. A compound according to claim 1, wherein $R_{13}$ and $R_{14}$ each independently represents —COOH, —$CONH_2$, —$CH_2OH$, or —CO—X, wherein X is an amino acid, or a peptide of 2–3 amino acids.

5. A compound selected from the group consisting of

Tyr($N^\alpha$Me)-Tic-Phe-Phe-OH (SEQ ID NO: 6);

H-Dmt-Tic-Phe-Phe-OH (SEQ ID NO: 10);

H-Dmt-Tic-Phe-Phe-$NH_2$ (SEQ ID NO: 11);

H-Tyr-TicΨ[$CH_2$—NH]Phe-Phe-OH (SEQ ID NO: 3)

H-Dmt-TicΨ[$CH_2$—NH]Phe-Phe-OH (SEQ ID NO: 15);

H-Dmt-TicΨ[$CH_2$—NH]Phe-Phe-$NH_2$ (SEQ ID NO: 16);

H-Tyr-Tic-Hfe-Phe-OH (SEQ ID NO: 2);

Tyr(NMe)-TicΨ[$CH_2$—NH]Hfe-Phe-OH (SEQ ID NO: 19);

H-Tyr-Tic-Atc-Phe-OH (SEQ ID NO: 25);

H-Tyr-Tic-Trp-Phe(p$NO_2$)-Tyr-Pro-Ser-$NH_2$ (SEQ ID NO: 32);

H-Tyr-TicΨ[$CH_2$—NH]Phe-OH;

H-Tyr-TicΨ[$CH_2$—$NCH_1$]Phe-Phe-OH (SEQ ID NO: 17);

H-Tyr-Tic-Phg-Phe-OH (SEQ ID NO: 20);

H-Tyr-Tic-His-Phe-OH (SEQ ID NO: 23);

H-Tyr-Tic-2-Nal-Phe-OH (SEQ ID NO: 24); and

H-Tyr-Tic-Phe-Phe-Val-Val-Gly-$NH_2$ (SEQ ID NO: 29).

6. A pharmaceutical composition comprising a compound according to claim 1 together with one or more pharmaceutical carriers.

7. A pharmaceutical composition comprising a compound according to claim 1 in an amount effective for inducing analgesia, together with a pharmaceutically acceptable carrier.

8. A pharmaceutical composition comprising a compound according to claim 1 in an amount effective for inducing immunosuppression, together with a pharmaceutically acceptable carrier.

9. A method for producing immunosuppressive effects whereby an effective amount of a compound according to claim 1 is administered to a patient in the need of such treatment.

10. A method for treating pain in a mammal suffering therefrom comprising administering to said mammal a compound of claim 1.

* * * * *